（12） United States Patent
Pigozzo et al.

(10) Patent No.: US 6,357,277 B1
(45) Date of Patent: Mar. 19, 2002

(54) METHOD AND EQUIPMENT FOR THE REALIGNMENT OF PEAKS IN GAS CHROMATOGRAPHIC ANALYSES

(75) Inventors: Fausto Pigozzo, Boffalora d'Adda; Pier Albino Colombo, Treviglio; Paolo Magni; Sorin Trestianu, both of Rodano, all of (IT)

(73) Assignee: Thermoquest Italia S.p.A., Rodano (IT)

( * ) Notice: Subject to any disclaimer, the term of this patent is extended or adjusted under 35 U.S.C. 154(b) by 0 days.

(21) Appl. No.: 09/404,928

(22) Filed: Sep. 24, 1999

(30) Foreign Application Priority Data

Feb. 25, 1999 (IT) .......................... MI99A0389

(51) Int. Cl.[7] .......................... B01D 15/08; B01D 53/14; G01N 21/00
(52) U.S. Cl. .......................... 73/23.22; 73/1.06; 73/1.16; 73/1.34; 95/82
(58) Field of Search .......................... 73/19.02, 54.02, 73/54.05, 54.06, 54.07, 23.22, 23.23, 23.24, 23.25, 23.26, 23.27, 64.55, 1.02, 1.03, 1.06, 1.16, 1.34, 1.35; 95/82, 87

(56) References Cited

U.S. PATENT DOCUMENTS

| | | | | |
|---|---|---|---|---|
| 4,976,750 A | * | 12/1990 | Munari | ........................ 95/82 |
| 5,405,432 A | * | 4/1995 | Snyder et al. | ................ 95/82 |
| 5,459,677 A | * | 10/1995 | Kowalski et al. | ............ 73/1.02 |
| 5,476,000 A | * | 12/1995 | Henderson et al. | ........ 73/23.27 |
| 5,637,790 A | * | 6/1997 | de Corral | ................ 73/54.06 |
| 5,938,817 A | * | 8/1999 | Shibamoto et al. | ........ 73/23.24 |

* cited by examiner

Primary Examiner—Michael Cygan
(74) Attorney, Agent, or Firm—Cobrin & Gittes

(57) ABSTRACT

The invention concerns a method for the realignment of peaks in gas chromatographic analyses after the replacement of the used capillary column with a nominally equal one, wherein a K coefficient characteristic of the column is preventively calculated by flowing carrier gas in the column under stabilized conditions of pressure and flow rate and of the column temperature, said K coefficient being stored in a memory of the gas chromatographic system. Said K coefficient is used to correlate at least two of the above mentioned parameters in subsequent analyses, obtaining an automatic realignment of peaks. The invention also concerns the analytical equipment to perform the method, and the capillary gas chromatographic column characterized as reported above.

9 Claims, 3 Drawing Sheets

METHOD AND EQUIPMENT FOR THE REALIGNMENT OF PEAKS IN GAS CHROMATOGRAPHIC ANALYSES

BACKGROUND OF THE INVENTION

1. Field of the Inventiuon

The present invention concerns a method, as well as the equipment designed to carry-out such a method, to obtain the reproducibility of the retention times of the components of a mixture analyzed in an instrument of gas chromatographic analysis, when the capillary column used is replaced with another nominally equal column in the same equipment or in different but nominally equal equipments operating under the same conditions.

The problem which underlies the present invention arises from the observation that the retention times of a given component in a mixture to be analyzed by gas chromatography show values which vary from column to column and from equipment to equipment, even if the nominal features of columns and equipments are exactly the same. This causes a shift along the axis of the chromatogram times of the peak related to the concerned component versus the same peak obtained in an identical analysis in a different, while nominally equal column.

2. Description of the Prior Art

It is known that the result of a gas chromatographic analysis is a chromatogram formed by a sequence of peaks, each indicating the arrival of a component of the analyzed mixture at a detector placed downstream of the column after a so-called retention time $t_r$, measured from the sample introduction into the column, and representing the time required to pass through the column.

The retention time $t_r$ obviously depends on the nature of the concerned component, on the nature and thickness of the stationary phase film present in the column and on the analytical procedures, particularly on the temperature program of the column and on the carrier gas pressures at the column inlet and outlet. The retention time $t_r$ is also affected, for the same component and under the same conditions, by the characteristics of the capillary column, particularly its length and diameter.

As a consequence, the variations in the retention times of the components of the same mixture, namely the peak shifts that are detected in equal analyses with different but nominally equal columns, depend on the different geometry of said columns.

In fact it was observed that nominally equal columns, i.e. having the same diameter and the same nominal length, actually have not negligible differences both in length and internal diameter, which obviously is not uniform and controllable on the entire extent of the column and varies from one column to the other.

These differences versus the nominal values create said peak shifts in identical analyses on different but nominally equal columns, in the same equipment or in different but nominally equal equipments. This shift involves the need, when replacing the column or changing the equipment, to change the parameters used for the recognition of peaks (peak tables), which means that it becomes necessary to modify the analytical method with waste of time, extra costs and failure to comply with GLP (Good Laboratory Practice) requirements.

To eliminate this drawback, it was already proposed to use a methodology named blocking of the retention time, which consists in the following procedure. A standard mixture is chosen and a reference analysis is run at a defined inlet pressure of carrier gas, identifying a reference compound and the relevant retention time. After the column replacement, analyses are run with the same mixture and at carrier gas inlet pressures equivalent to 80%, 90%, 100%, 110% and 120% respectively of the previously used inlet pressure, acquiring the retention times for the reference compound. Then a graph is plotted, indicating the retention times as a function of the inlet pressure and joining the points plotted with straight line segments. Then the original retention time is entered in the graph to obtain the new inlet pressure that must be maintained in the subsequent analyses to obtain the realignment of peaks.

This method, however, is rather time-consuming and complicated. Moreover, it allows the realignment of peaks only when these are close to that of the reference compound. But the most serious inconvenience is that this method requires all subsequent analyses to be carried out in the constant pressure analytical mode, whereas running analyses according to the carrier constant flow rate mode is more advantageous as far as detector response and total analytical time are concerned.

OBJECTS OF THE INVENTION

Assuming that, when the column is replaced or the equipment changed, the geometry of the new column is responsible of the peak shift, i.e. of the variations of retention times, the Applicant has resolved to apply a method that allows to automatically characterize each column used, keeping into consideration the actual values of length and internal diameter of same, and to use such characterization to obtain an automatic realignment of all peaks, without differences caused by their position on the chromatogram, whatever the analytical mode selected (feeding of carrier gas at constant or programmed flow rate, or at constant or programmed pressure).

DESCRIPTION OF THE PREFERRED EMBODIMENTS

The procedures of use and the characteristics of the invention will be now described with reference to preferred embodiments and to the accompanying drawings, where:

FIG. 1 is a diagram showing the meaning of the characterization constant K through the correlation between $F_m$ and $$\frac{p_{in}^2 - p_{out}^2}{Tc^{1+\alpha}}$$

value.

The K constant mentioned in the main claim is obtained from the known Poiseuille's equation which correlates pressure and flow rate of gases in capillary ducts, said equation being modified to keep into account the fact that the mass flow rate $F_m$ of the carrier gas is conventionally expressed as volumetric flow rate in standard conditions ($p_{std}=1$ atm; $T_{std}=298°$ K.):

$$F_m = \frac{\pi d^4}{256 L} \frac{T_{std}^{1+\alpha}}{p_{std} \eta_{std}} \frac{p_{in}^2 - p_{out}^2}{T_c^{1+\alpha}}$$

where d: is the actual inner diameter of the gas chomatographic column, equivalent to the inner diameter of an ideal cylindrical column having a length L and an internal volume equal to that of the real column;

L: is the actual length of the column $T_{std}$: is the standard temperature ($T_{st}=298°$ K.)

$p_{std}$: is the standard pressure ($P_{std}=1$ atm)

$\eta_{std}$: is the viscosity of carrier gas under standard pressure and temperature conditions $p_{in}$: is the absolute pressure of carrier gas at the column inlet $p_{out}$: is the absolute pressure of carrier gas at the column outlet, generally corresponding to 1 atm (0 atm when the outlet is under vacuum)

$T_c$: is the column actual temperature $\alpha$: is an experimental coefficient depending on the carrier gas nature In the previous formula, taking $$K = \frac{\pi d^4}{256 L} \frac{T_{std}^{1+\alpha}}{p_{std} \eta_{std}} \quad (2)$$

the result is $$F_m = K \frac{p_{in}^2 - p_{out}^2}{T_c^{1+\alpha}} \quad (3)$$

Therefore it is obvious that the K coefficient, comprising constant and known terms such as $T_{std}$, $p_{std}$, $\eta_{std}$ and $\alpha$, depends on the actual values of the column inner diameter and length and can be assumed as a parameter indicating such geometrical measures and therefore be correlable to the retention time of the components of a mixture in that concerned specific column.

Said K coefficient can be obtained using the equation (3), by making a carrier gas pass through the column and measuring, under stabilized conditions of carrier gas flow through the column, the values $T_c$, $F_m$, $p_{in}$ and possibly pout. It should be noted that $p_{out}$ is generally equal to 0 or 1 atm, and therefore it can be set without any measurement. The result is:

$$K = \frac{F_m T_c^{1+\alpha}}{p_{in2} - p_{out2}} \quad (4)$$

For more precision, it is possible to repeat the above measures, varying by steps the inlet pressure and measuring the carrier mass flow rate, always at a constant temperature $T_c$.

It is also evident that if a small quantity of sample together with carrier should cross the column, instead of carrier gas alone, the situation would not change and the results would be practically the same.

Figure 1:
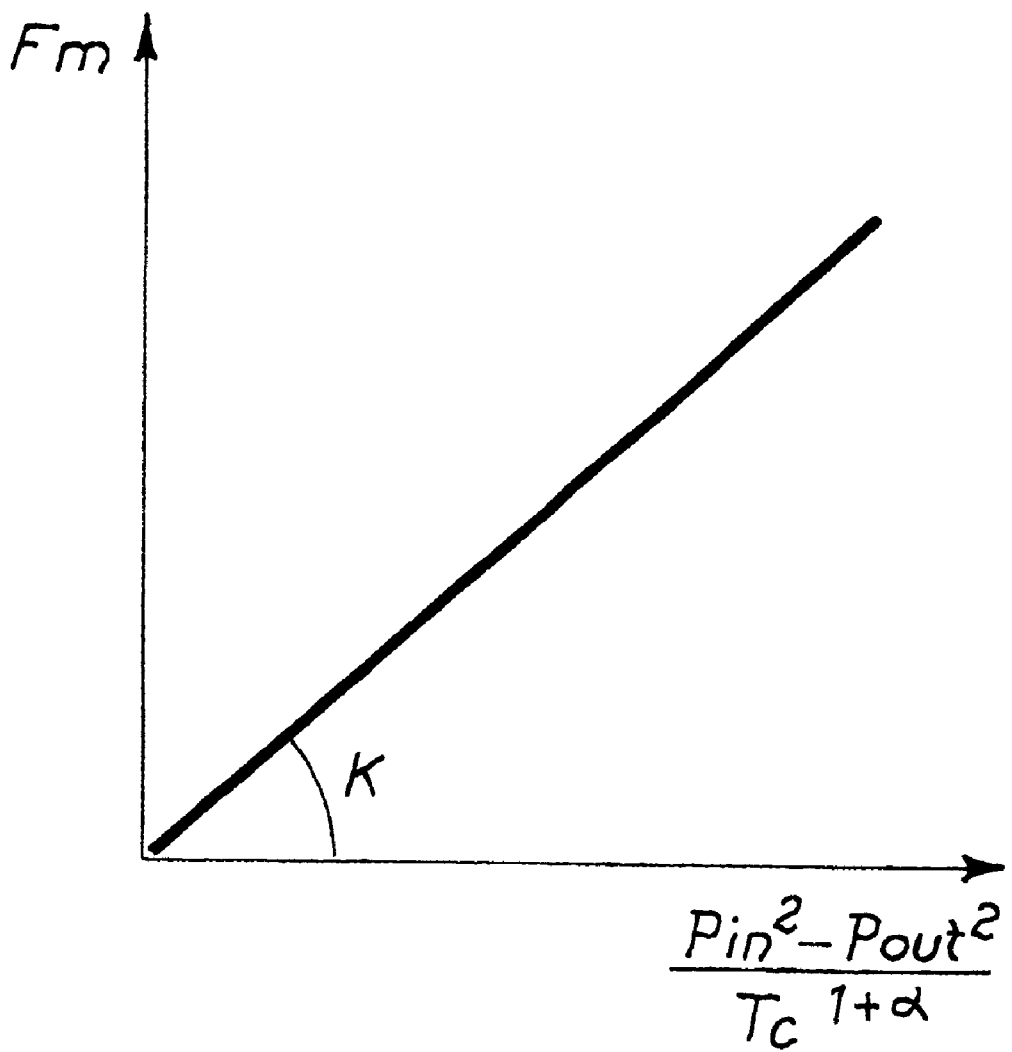

The K coefficient is therefore equal to the angular coefficient of the straight line that corrrlates $F_m$ in ordinates, and $$\frac{p_{in}^2 - p_{out}^2}{T_c^{1+\alpha}}$$

in abscissae, reported in the accompanying FIG. 1.

To keep into consideration the real dimensions of the column, the calculated K coefficient is stored in the memory of the system controlling the gas chromatograph. Afterwards, it will be sufficient to use such K coefficient to correlate at least two of the control parameters (carrier gas inlet pressure $p_{in}$ and mass flow rate $F_m$, and column temperature $T_c$) of the subsequent analyses run with the same column. The realignment of peaks is ensured by the fact that, when replacing a column with another, nominally equal to the first one, the characterization procedure is repeated and a new K value is obtained, which automatically keeps into account the real dimensions of the new column.

The realignment of retention times derives from the fact that the retention time $t_r$ is the sum of two elements: the time elapsed in the stationary phase $t_{staz}$, when the component is immobile, and the time elapsed in the mobile phase $t_m$, when the component is carried by carrier gas:

$$t_r + t_{staz}$$

If the nature and thickness of the stationary phase are the same in nominally equal columns (as supposedly it should be), and the temperature program is the same, the variation in retention time $\Delta t_r$ is equal to the variation in the time elapsed in the mobile phase (carrier):

$$\Delta t_r = \Delta t_m$$

The variation $\Delta t_m$ can be expressed as a function of the variation of carrier gas flow rate and also of the column geometry:

$$\Delta t_m = F (\Delta F_m, \Delta L, \Delta d)$$

It was observed that the variation in carrier gas flow rate is predominant versus the other variations, and therefore if the flow rate is maintained strictly constant from column to column, the variation in retention time is limited. If on the contrary, the operation mode is at constant inlet pressure, the flow rate variation resulting from the variation of the column parameters causes a considerable variation of the retention time.

This can be explained by equations (2) and (3), which show that the flow rate variation is proportional to the variation of the column diameter raised to the fourth power, and therefore a small variation in diameter results in important variations in flow rate.

In practice, equation (3) is used again, where the K coefficient, previously determined during the column characterization, is used to control one of the parameters that control the analysis, according to the operating requirements.

When the desired operating mode is at carrier constant flow rate, in equation (3) the desired value of flow rate will be introduced and inlet pressure calculated, according to the K value previously calculated and stored and to the column temperature, which varies moment by moment. The resulting chromatogram will automatically keep into account the geometrical features of the column, performing the desired realignment of peaks.

The same occurs when the analysis is run according to a programmed variation of the carrier gas flow rate, with the only difference that the pressure calculation will no longer be related to a value of constant flow rate, but to the desired value of flow rate moment by moment.

If, during an analysis with a new column nominally equal to the previous one, the desired operating mode is at constant or programmed pressure, the inlet pressure required to obtain the same flow rate in the second column, at constant temperature, must be calculated. Such inlet pressure will vary in relation to the variation of the K coefficient values between the two columns. By setting the calculated pressure, also in this case, the result is a realignment of peaks in the two columns.

Figure 2:
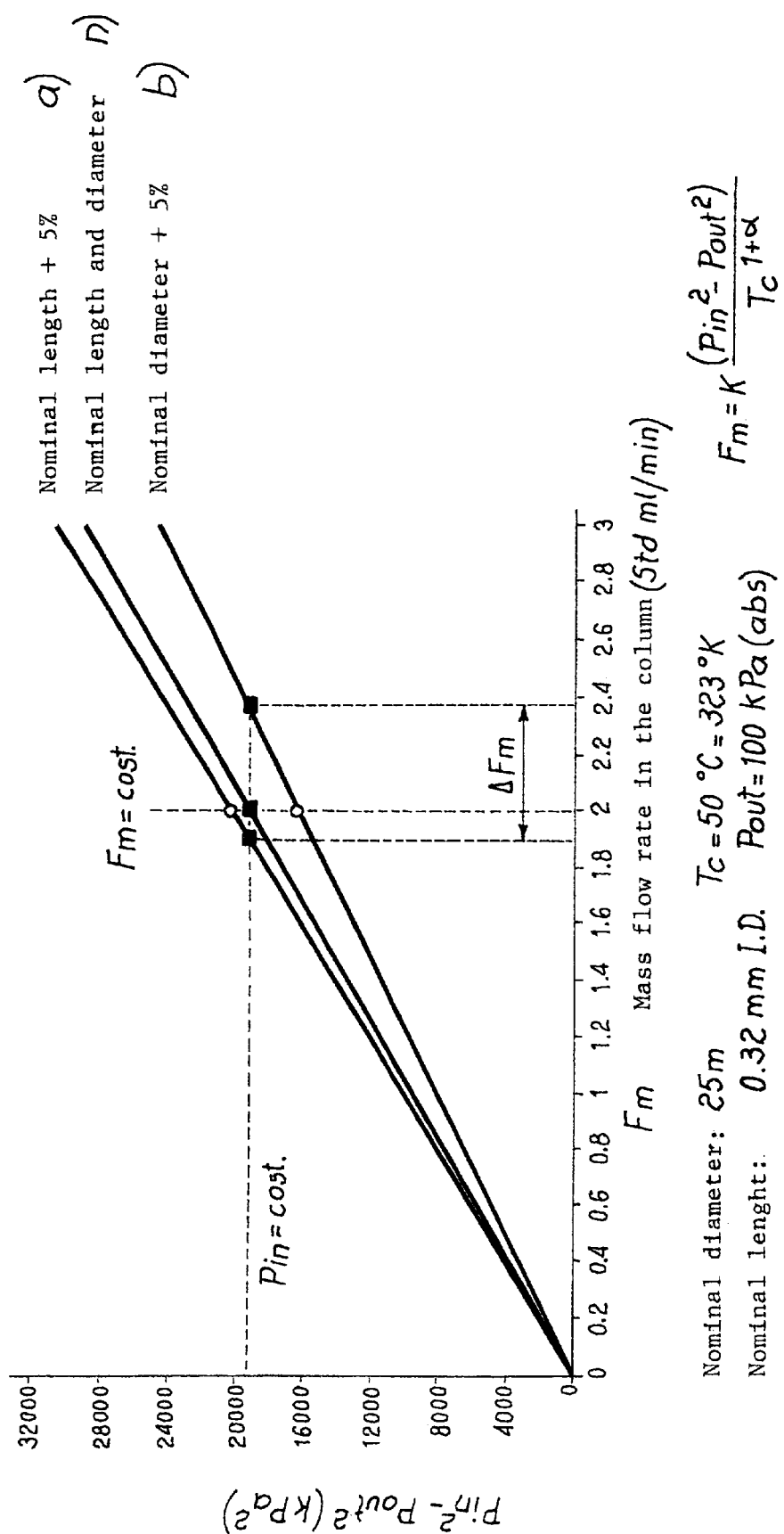
FIG. 2 is a diagram showing the correlation between carrier inlet pressure $p_{in}$ and carrier mass flow rate $F_m$ through the column at constant temperature.

FIG. 2 reports a diagram with the variations of carrier mass flow rate $F_m$, in abscissae, and of $p_{in}^2 - p_{out}^2$, calculated respectively for a column (n) having nominal length of 25 m and nominal inner diameter of 0.32 mm, for a column (a) of the same diameter, but 5% longer, and for a column (b) of the same length but with internal diameter 5% larger, the whole at a temperature $T_c=50°$ C. and absolute outlet pressure of 100 kPa. It is observed that, with the same inlet pressure pin, flow rate variations between the two nominally equal columns a) and b) are about 0.5 ml/min.

The following table 1 reports the results of a series of analyses performed on the same mixture, in the same gas chromatographic equipment, with nominally equal but actually different columns. Analyses were run at constant flow rate (1.2 ml/min) programming the column temperature first with an increase from 50° C. to 100° C. at 50° C./min rate, then with an increase from 100° C. to 250° C. at 30° C./min rate and finally with an increase from 250° C. to 340° C. at 20° C./min rate.

TABLE I

VARIATIONS IN RETENTION TIMES FROM COLUMN TO COLUMN (Fm = const)

| | | Average Retention Times (min.) | | | | | | | | |
|---|---|---|---|---|---|---|---|---|---|---|
| | | nC6 | nC8 | nC10 | nC12 | nC14 | nC18 | nC20 | nC28 | nC32 | nC36 |
| COLUMN 1 (K = 1.83088) | | 2.102 | 2.573 | 3.348 | 4.251 | 5.139 | 5.955 | 7.443 | 10.275 | 11.698 | 13.783 |
| COLUMN 2 (K = 1.73161) | | 2.086 | 2.554 | 3.325 | 4.226 | 5.112 | 5.928 | 7.414 | 10.243 | 11.657 | 13.719 |
| Differences in | min | 0.016 | 0.019 | 0.023 | 0.025 | 0.027 | 0.026 | 0.029 | 0.031 | 0.039 | 0.064 |
| Retention Times | % | 0.78 | 0.76 | 0.68 | 0.59 | 0.52 | 0.44 | 0.39 | 0.30 | 0.34 | 0.46 |

Average of 10 consecutive tests
TRACE GC EQUIPMENT
In-column flow rate: 1.2 ml/min (CF)
Column initial pressure 1: 14.4 psi
Column initial pressure 2: 13.9 psi The K coefficients of the two columns were calculated to control the steadiness of the flow rate through the inlet pressure, and the retention times for different components were detected. It can be noted that the variations in retention times are ranging approximately from 1 to 4 seconds and, as a percentage, they are always below 1%.

What above was repeated in case of installation of nominally equal columns in analytical equipments of the same type but different from each other, obtaining the results reported in the following table 2.

TABLE II

VARIATIONS IN RETENTION TIMES FROM EQUIPMENT TO EQUIPMENT (Fm = const)

| | | Average Retention Times (min.) | | | | | | | | |
|---|---|---|---|---|---|---|---|---|---|---|
| | | nC6 | nC8 | nC10 | nC12 | nC14 | nC18 | nC20 | nC28 | nC32 | nC36 |
| GC Equipment 1 Column 1 | | 2.102 | 2.573 | 3.348 | 4.251 | 5.139 | 5.955 | 7.443 | 10.275 | 11.698 | 13.783 |
| GC Equipment 2 Column 3 | | 2.082 | 2.568 | 3.337 | 4.244 | 5.135 | 5.953 | 7.441 | 10.270 | 11.681 | 13.773 |
| Differences in | min | 0.020 | 0.015 | 0.011 | 0.008 | 0.004 | 0.002 | 0.002 | 0.005 | 0.015 | 0.010 |
| Retention Times | % | 0.98 | 0.60 | 0.32 | 0.18 | 0.08 | 0.08 | 0.02 | 0.04 | 0.13 | 0.07 |

Figure 3:
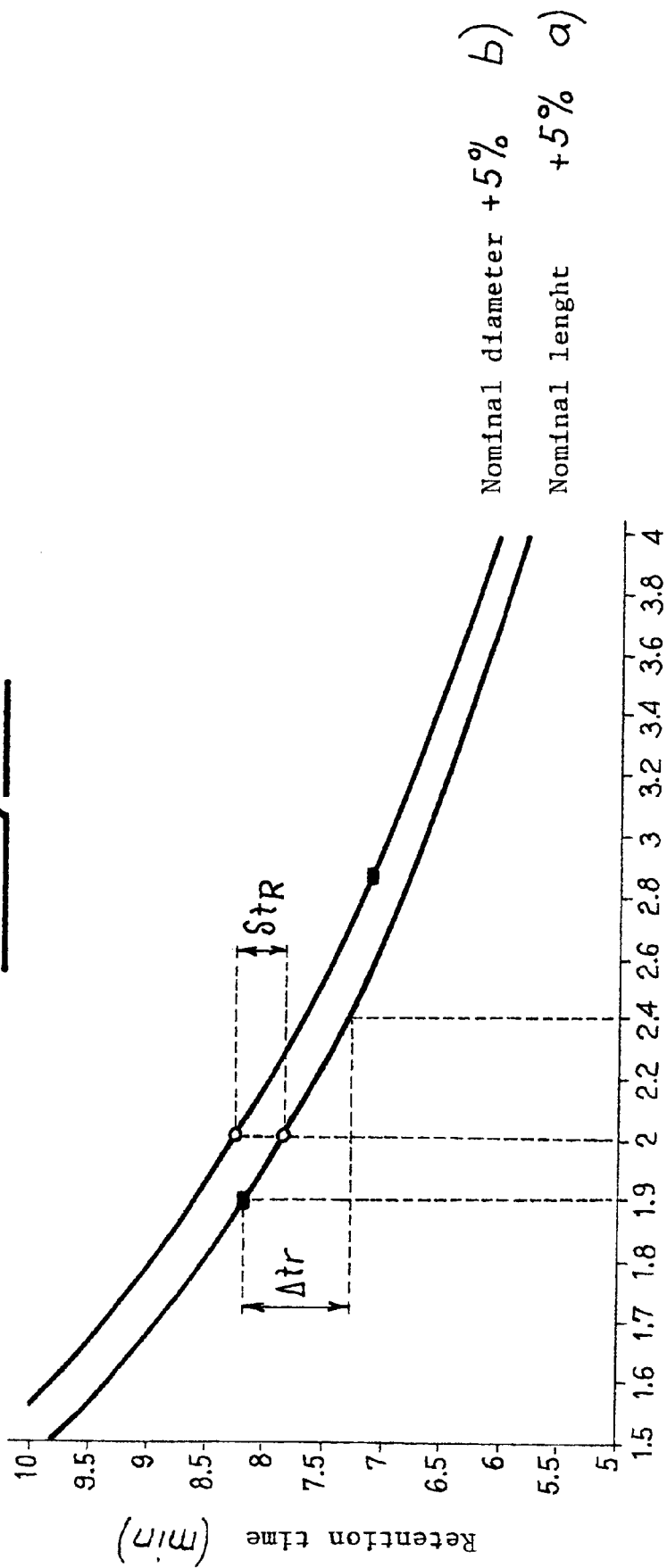
FIG. 3 is a diagram showing the variations of the retention time as a function of the mass flow rate $F_m$ at constant temperature for two columns having lengths and diameters different from their nominal value.

Average of 10 consecutive tests
In-column flow rate: 1.2 ml/min (CF)
Column initial pressure 1: 14.4 psi
Column initial pressure 3: 14.5 psi FIG. 3 shows the variations of the retention time versus the carrier mass flow rate Fm for the same two columns (a) and (b) of FIG. 2. It can be seen that, when the flow rate remains constant (2 std ml/min), the variation in retention time δtr, for a given component and at constant temperature, remains limited.

By keeping the inlet pressure constant in the two actually different but nominally equal columns (a) and (b), the actual flow rates of carrier gas vary from about 1.9 to 2.45 std ml/min (see FIG. 2) and this results in a considerably higher variation (see FIG. 3) of the retention time (Δtr).

The results show that in this case too the method used allows to limit the variation of retention times within 1%.

For the application of the method of the invention, the gas chromatographic equipment, besides the usual components, shall be equipped with carrier gas pressure and flow sensors, as well as electronic means to calculate and store the K coefficient and to use said K coefficient in the control of subsequent analyses.

Preferably, the equipment is provided with a function, activated for instance through a push-button, to automatically perform the column characterization by carrying-out a passage through the column of carrier gas under controlled conditions, with detection of the values of flow rate, pressure and temperature, and with consequent calculation and storage of the K coefficient.

From the above reported description it can be noted that the K coefficient practically represents a parameter that characterizes the fluid-dynamic behavior of a column, and therefore each column can be identified and characterized, together with the other parameters, also from its K coefficient.

This means that it can be assumable that each column be assigned such K parameter to characterize the column itself, introducing it into an appropriate gas chromatographic equipment, to calculate as said above, its K coefficient. This coefficient can then be made explicit and assigned, with other identifying elements, to the concerned column.

In a similar case, to obtain the desired realignment of peaks, when installing a column for running analyses, it will be sufficient to enter the K value of the column in the system and operate as above described, controlling the analytical parameters through the K coefficient.

If, with the column installed, the column is characterized again obtaining a new K coefficient significantly different from the original one, this would mean that the column has undergone geometrical modifications, or that, after its installation into the gas chromatographic system, carrier gas leaks or hydraulic clogging have occurred.

What is claimed is:

1. A method for obtaining the reproducibility of the retention times of the components of a mixture analyzed in a gas chromatographic equipment after the replacement of the used capillary column with a nominally equal one, characterized by the following steps:

I) calculating a K coefficient characteristic of the column by flowing through the column carrier gas under stabilized conditions of carrier gas pressure and flow rate and of the column temperature, measuring parameter values of the carrier gas pressure at column inlet ($P_{in}$), of carrier gas mass flow rate ($F_m$) and of the column temperature ($T_c$), and measuring or setting the carrier gas pressure at column outlet ($P_{out}$), and entering such values in the following equation:

$$K = \frac{F_m T_c^{1+\alpha}}{p_{in}^2 - p_{out}^2}$$

where:
α is a settable experimental exponent, depending on the carrier gas nature;

II) storing said K coefficient in a memory of the gas chromatographic equipment; and III) using said K coefficient to correlate at least two of above mentioned parameters in subsequent analyses.

2. A method according to claim 1, characterized in that the parameters correlated through said K coefficient are the carrier gas inlet pressure and flow rate.

3. A method according to claim 2, characterized in that said K coefficient is used to correlate the carrier gas inlet pressure and flow rate, by keeping the flow rate at a constant value or at values that follow a predefined curve, through the carrier gas inlet pressure programming, as the column temperature changes.

4. A method according to claim 2, characterized in that said K coefficient is used to correlate the carrier gas inlet pressure and flow rate in two different but nominally equal columns in order to calculate inlet pressures at equal and constant flow rate, and to use the calculated pressure for a second column, in analyses run under constant or programmed pressure conditions.

5. An apparatus for gas chromatographic analysis comprising means for heating at a temperature a capillary gas chromatographic column, an injector for introducing into the column a mixture to be analyzed, a detector for detecting at a column outlet a passage of analyzed mixture components, means for feeding a carrier gas to said column, means for detecting temperature conditions, of the column and carrier gas inlet pressure, an electronic system for control of equipment, characterized by a sensor of the carrier gas flow rate in the column; means for calculating a K coefficient on the basis of information obtained by measuring the values of the carrier gas pressure at the column inlet ($p_{in}$), of carrier gas mass flow rate ($F_m$), of column temperature ($T_c$) and measuring or setting the carrier gas pressure at the column outlet ($p_{out}$) during a passage of carrier gas under constant and stabilized conditions of column temperature, of carrier gas pressure and flow rate, which information is supplied by temperature, pressure and flow detecting devices, and entering such values in the following equation:

$$K = \frac{F_m T_c^{1+\alpha}}{p_{in}^2 - p_{out}^2}$$

where:
α is a settable experimental exponent, depending on the carrier gas nature; means for storing in a memory the calculated K coefficient; and means for controlling analytical conditions using the stored K coefficient.

6. An apparatus according to claim 5, characterized by means for performing calculate and store said K coefficient.

7. A method for the characterization of a capillary column for a gas chromatographic equipment in relation with a given carrier gas wherein a) the column is mounted in a gas chromatographic equipment;

b) a K coefficient characteristic of the column is calculated by flowing through the column said carrier gas under stabilized conditions of gas pressure and flow rate and of column temperature, measuring parameter values of the carrier gas pressure at column inlet ($p_{in}$), of carrier gas mass flow rate ($F_m$) and of the column temperature ($T_c$), and measuring or setting the carrier gas pressure at column inlet ($p_{out}$), and entering such values in the following equation:

$$K = \frac{F_m T_c^{1+\alpha}}{p_{in}^2 - p_{out}^2}$$

where:
α is a settable experimental exponent, depending on the carrier gas nature, and c) assigning the obtained K coefficient to said column by means of labelling.

8. A method for obtaining the reproducibility of the retention times of the components of a mixture analyzed in a gas chromatographic equipment after the placement of the used capillary column with a nominally equal one, characterized by the following steps:

a) using a new column;

b) setting in the gas chromatographic system the value of a K coefficient related to said new column by measuring the values of the carrier gas pressure at the column inlet ($p_{in}$), of the carrier gas mass flow rate ($F_m$), of the column temperature ($T_c$) and measuring or setting the carrier gas pressure at the column outlet ($p_{out}$) during a passage of carrier gas through said column under stabilized conditions of column temperature, of carrier gas pressure and flow rate, and entering such values in the following equation:

$$K = \frac{F_m T_c^{1+\alpha}}{p_{in}^2 - p_{out}^2}$$

where:
$\alpha$ is a settable experimental exponent, depending on the carrier gas nature; and
c) storing and using said K coefficient to correlate in subsequent analysis at least two parameters selected from a group consisting of carrier gas pressure and flow rate and column temperature.

9. A method to check for a presence of leaks or clogging in a hydraulic circuit of a column that is downstream of a carrier gas regulating system, said method comprising:
a) associating an original value of a K coefficient with the column installed which is calculated by measuring the values of the carrier gas pressure at the column inlet ($p_{in}$), of carrier gas mass flow rate ($F_m$), of column temperature ($T_c$) and measuring or setting the carrier gas pressure at the column outlet ($p_{out}$) during a passage of carrier gas through said column under stabilized conditions of column temperature, of carrier gas pressure and flow rate, and entering such values in the following equation:

$$K = \frac{F_m T_c^{1+\alpha}}{p_{in}^2 - p_{out}^2}$$

where:
$\alpha$ is a settable experimental exponent, depending on the carrier gas nature;
b) determining an experimental value of the K coefficient at the same way specified in step a) and storing said value;
c) comparing said experimental value with the original value associated with the
d) checking for the presence of leaks or clogging in the hydraulic circuit of the column based on results from the comparing.

* * * * *